US00PP17494P2

(12) United States Plant Patent
Mineo

(10) Patent No.: US PP17,494 P2
(45) Date of Patent: Mar. 13, 2007

(54) ***GAURA* PLANT NAMED 'PINK LADY'**

(50) Latin Name: *Gaura lindheimeri*
Varietal Denomination: Pink Lady

(76) Inventor: Baldassare Mineo, 2825 Cummings Rd., Medford, OR (US) 97501

( * ) Notice: Subject to any disclaimer, the term of this patent is extended or adjusted under 35 U.S.C. 154(b) by 0 days.

(21) Appl. No.: 11/204,329

(22) Filed: Aug. 15, 2005

(51) Int. Cl.
*A01H 5/00* (2006.01)

(52) U.S. Cl. ..... Plt./226
(58) Field of Classification Search ..... Plt./226, Plt./263
See application file for complete search history.

*Primary Examiner*—Kent Bell
(74) *Attorney, Agent, or Firm*—C. A. Whealy

(57) ABSTRACT

A new and distinct cultivar of *Gaura* plant named 'Pink Lady', characterized by its upright, compact and mounded plant habit; freely branching growth habit; dense and bushy appearance; short flowering stems; flowers positioned just above the foliage; freely flowering habit; long flowering period; and pink-colored flowers.

2 Drawing Sheets

Botanical designation: *Gaura lindheimeri.*
Cultivar denomination: 'Pink Lady'.

BACKGROUND OF THE INVENTION

The present Invention relates to a new and distinct cultivar of *Gaura* plant, botanically known as *Gaura lindheimeri,* and hereinafter referred to by the cultivar name Pink Lady.

The new *Gaura* originated from a random pollination of two unnamed selections of *Gaura lindheimeri,* not patented. The new *Gaura* was discovered and selected by the Inventor as a single plant from the resulting progeny of the random pollination in June, 2001 in an controlled environment in Medford, Oreg.

Asexual reproduction of the new cultivar by terminal cuttings in a controlled environment in Medford, Oreg. since July, 2001, has shown that the unique features of this new *Gaura* are stable and reproduced true to type in successive generations.

SUMMARY OF THE INVENTION

Plants of the cultivar Pink Lady have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Lady'. These characteristics in combination distinguish 'Pink Lady' as a new and distinct cutlivar of *Gaura:*

1. Upright, compact and mounded plant habit.
2. Freely branching growth habit; dense and bushy appearance.
3. Short flowering stems; flowers positioned just above the foliage.
4. Freely flowering habit.
5. Long flowering period.
6. Pink-colored flowers.

Plants of the new *Gaura* differ from plants of the parent selections primarily in flower color and plant habit.

Plants of the new *Gaura* can be compared to plants of the *Gaura* cultivar Siskiyou Pink, not patented. In side-by-side comparisons conducted in Medford, Oreg., plants of the new *Gaura* differed from plants of the cultivar Siskiyou Pink in the following characteristics:

1. Plants of the new *Gaura* had shorter flowering stems than plants of the cultivar Siskiyou Pink.
2. Plants of the new *Gaura* had lighter pink-colored flowers than plants of the cultivar Siskiyou Pink.

Plants of the new *Gaura* can also be compared to plants of the *Gaura* cultivar Blushing Butterflies, not patented. In side-by-side comparisons conducted in Medford, Oreg., plants of the new *Gaura* differed primarily from plants of the cultivar Blushing Butterflies in plant height as plants of the new *Gaura* were taller than plants of the cultivar Blushing Butterflies.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Gaura.*

The photograph on the first sheet comprises a side perspective view of typical flowering plants of 'Pink Lady' grown in a container.

The photograph on the second sheet is a close-up view of typical flowers of 'Pink Lady'.

DETAILED BOTANICAL DESCRIPTION

The aforementioned photographs and following observations and measurements describe plants grown in Medford, Oreg. in an outdoor nursery during the summer with temperatures ranging 4° C. to 35° C. Plants were grown in containers and had been growing for about 18 months when the photographs and description were taken. Plants were pinched one time. Color references are made to The Royal Horticultural Society Colour Chart, 1995 Edition, except where general terms of ordinary dictionary significance are used.

Botanical classification: *Gaura lindheimeri* cultivar Pink Lady.

Parentage: Random pollination of two unnamed selections of *Gaura lindheimeri,* not patented.

Propagation:

*Type cutting.*—Vegetative cuttings.

*Time to initiate roots, summer.*—About 21 days at 25° C.

*Time to initiate roots, winter.*—About 30 days at 10° C.

*Time to produce a rooted young plant, summer.*—About three months at 25° C.

*Time to produce a rooted young plant, winter.*—About six months at 10° C.

*Root description.*—Thick, fibrous, fleshy; white in color.

Plant description:

*Form.*—Upright, compact and mounded plant habit; broad inverted triangle; short flowering stems with flowers positioned just above the foliage. Freely branching growth habit; dense and bushy appearance. Vigorous growth habit.

*Plant height.*—About 60 to 75 cm.

*Plant diameter.*—About 75 cm.

*Lateral branches.*—Length: About 60 to 75 cm. Diameter: About 2 mm. Internode length: About 6 cm. Strength: Strong. Texture: Pubescent. Color: 137B to 137C.

*Foliage description.*—Arrangement: Alternate; simple; sessile. Length: About 5 cm. Width: About 5 mm. Shape: Lanceolate. Apex: Acute. Base: Acuminate. Margin: Spinulose to serrate. Texture, upper surface: Smooth, glabrous. Texture, lower surface: Slightly pubescent. Venation pattern: Pinnate. Color: Developing and fully expanded foliage, upper surface: 137B, mottled with 187A. Developing and fully expanded foliage, lower surface: 137B. Venation, upper surface: 146C. Venation, lower surface: 137A.

Flower description:

*Flower type and habit.*—Solitary zygomorphic flowers arranged on terminal and axillary spikes; flowers sessile. Flowers face mostly outwardly from the stem axis.

*Quantity.*—Freely flowering; terminal panicles with about 20 to 30 flowers per inflorescence.

*Natural flowering season.*—Long flowering period; plants typically flower from the spring throughout the summer in Oregon; flowering continuous during this period. Plants start flowering about four weeks after planting.

*Flower longevity on the plant.*—About two days; flowers not persistent.

*Fragrance.*—Slight.

*Inflorescence length.*—About 20 cm.

*Inflorescence diameter.*—About 5 cm.

*Flower size.*—Diameter: About 3 cm. Depth: About 3 cm.

*Flower buds.*—Length: About 1.5 cm. Diameter: About 4 mm. Shape: Ovate. Color: 187A.

*Petals.*—Quantity/arrangement: Four petals in a single whorl. Length: About 2 cm. Width: About 1 cm. Shape: Elliptic. Apex: Acute. Base: Attenuate. Margin: Entire. Texture, upper and lower surfaces: Smooth, satiny. Color: When opening and fully opened, upper surface: Close to 155C overlain with 55B; towards the margins and base, more heavily overlain with 55B; venation, 55B. When opening and fully opened, lower surface: 55A.

*Sepals.*—Arrangement/appearance: Single whorl of four sepals; fused at the base. Calyx length: About 1.6 cm. Calyx diameter: About 5 mm. Shape: Lanceolate. Apex: Acute. Base: Fused. Margin: Entire. Texture, upper and lower surfaces: Pubescent. Color, upper and lower surfaces: Close to 137B.

*Peduncles.*—Length: About 10 to 15 cm. Diameter: About 2 mm. Strength: Moderately strong. Texture: Smooth, glabrous. Color: Close to 147B.

*Reproductive organs.*—Stamens: Quantity per flower: Eight. Anther shape: Linear; slender. Anther length: About 2.5 mm. Anther diameter: About 0.5 mm. Anther color: 187A. Pollen color: 10A.

*Pistils.*—Quantity per flower: One. Pistil length: About 1.5 cm. Stigma shape: Four-parted. Ovary color: 187A.

*Fruit/seed.*—Fruit and seed production has not been observed.

Disease/pest resistance: Plants of the new *Gaura* have not been noted to be resistant to pathogens or pests common to *Gaura*.

Temperature tolerance: Plants of the new *Gaura* have been observed to tolerate temperatures from −10° C. to 35° C.

It is claimed:

1. A new and distinct cultivar of *Gaura* plant named 'Pink Lady', as illustrated and described.

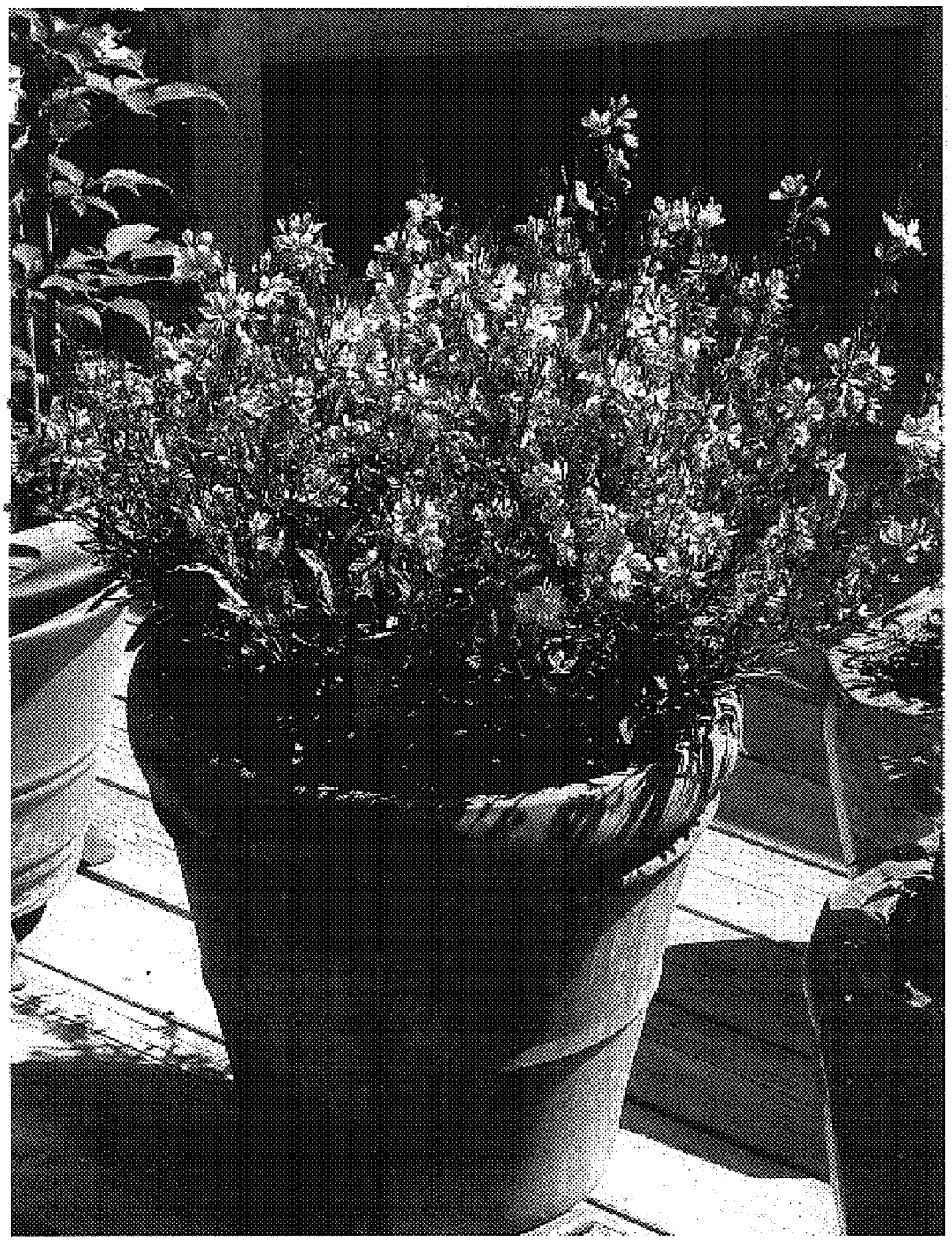

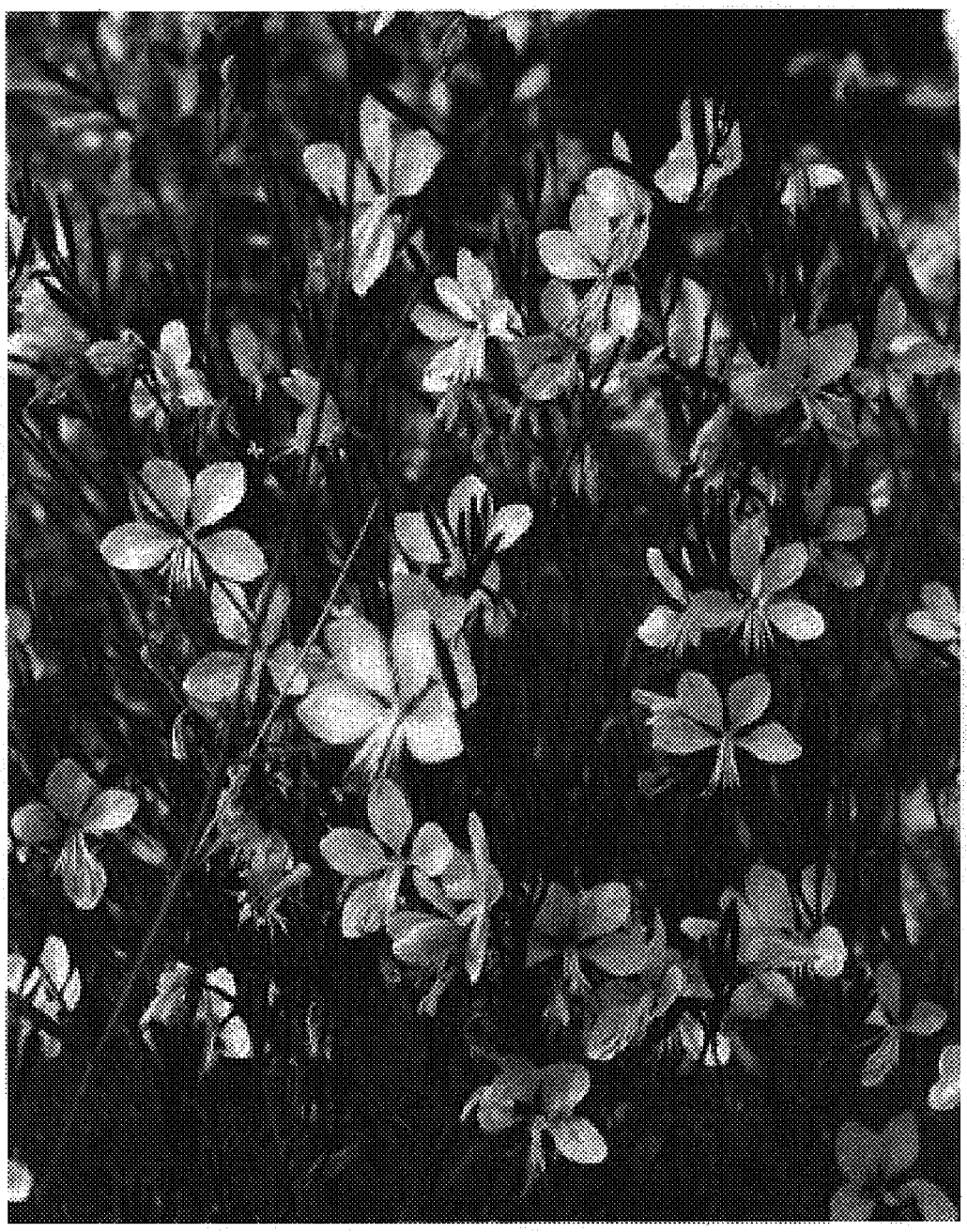

* * * * *